(12) United States Patent
Bascour et al.

(10) Patent No.: US 9,076,971 B2
(45) Date of Patent: Jul. 7, 2015

(54) SPIROBIFLUORENE COMPOUNDS

(75) Inventors: Dominique Bascour, Grez-Doiceau (BE); Jean-Pierre Catinat, Waudrez (BE)

(73) Assignee: SOLVAY (SOCIETE ANONYME), Brussels (BE)

( * ) Notice: Subject to any disclaimer, the term of this patent is extended or adjusted under 35 U.S.C. 154(b) by 34 days.

(21) Appl. No.: 13/878,421

(22) PCT Filed: Oct. 7, 2011

(86) PCT No.: PCT/EP2011/005013
§ 371 (c)(1),
(2), (4) Date: Aug. 15, 2013

(87) PCT Pub. No.: WO2012/048819
PCT Pub. Date: Apr. 19, 2012

(65) Prior Publication Data
US 2013/0324741 A1 Dec. 5, 2013

(30) Foreign Application Priority Data

Oct. 11, 2010 (EP) .................... 10187159
Sep. 28, 2011 (EP) .................... 11007866

(51) Int. Cl.
*C07C 25/22* (2006.01)
*C07C 255/52* (2006.01)
*H01L 51/00* (2006.01)
*C07F 5/02* (2006.01)
*H05B 33/20* (2006.01)
*H01L 51/50* (2006.01)

(52) U.S. Cl.
CPC ............ *H01L 51/0058* (2013.01); *C07C 25/22* (2013.01); *C07C 255/52* (2013.01); *C07C 2103/94* (2013.01); *C07F 5/025* (2013.01); *C09K 2211/185* (2013.01); *H01L 51/0072* (2013.01); *H01L 51/0073* (2013.01); *H01L 51/5016* (2013.01); *H01L 51/5048* (2013.01); *H05B 33/20* (2013.01)

(58) Field of Classification Search
CPC .............................. C07C 25/22; C07C 255/52
USPC ......................................................... 570/183
See application file for complete search history.

(56) References Cited

U.S. PATENT DOCUMENTS

2001/0015614 A1    8/2001    Taguchi et al.

FOREIGN PATENT DOCUMENTS

| JP | 2006-089585 A | 4/2006 |
| WO | WO-2010/108579 A1 | 9/2004 |
| WO | WO-2010/015306 A1 | 2/2010 |

OTHER PUBLICATIONS

Cheng, et al. Document No. 145:314635, retrieved from STN. (2006).*
Lee, et al. Document No. 143:78615, retrieved from STN. (2005).*
Avilov et al. (2004) "Quantum-Chemical Design of Host Materials for Full-Color Triplet Emission," Adv. Mater., 16(18):1624-1629.
Lee et al. (2003) "Synthesis of regio- and stereoselective alkoxy-substituted spirobifluorene derivatives for blue light emitting materials," Tetrahedron, 59:2773-2779.
Cheng et al. (2006) "A general synthetic route to chiral dihydroxy-9,9'-spirobifluorenes," Tetrahedron, 62:8077-8082.
Fournier et al. (2004) "Molecular Tectonics. Porous Hydrogen-Bonded Networks Built form Derivatives of 9,9'-Spirobifluorene," J. Org. Chem., 69:1762-1775.
Xie et al. (2010) "Spiro-functionalized ligand with supramolecular steric hindrance to control π-π interaction in the iridium complex for high performance electrophosphorescent devices," J. Phys. Chem. Lett., 1:272-276.

* cited by examiner

*Primary Examiner* — Shawquia Jackson

(57) ABSTRACT

Novel substituted spirobifluorene compounds useful as intermediates for materials in organic electronics devices 11 Claims, No Drawings

SPIROBIFLUORENE COMPOUNDS

The present invention relates to novel spirobifluorene compounds suitable for the manufacture of materials for applications in the area of organic electronics.

An important characteristic that must be optimized in the development of low molecular weight organic materials for application in the field of organic electronics is the ability to form morphologically stable amorphous films. The thermal stress undergone during device operation can indeed lead to phase transitions of the metastable amorphous film into a thermodynamically stable polycrystalline state. The crystallisation induces a fast degradation of the performance of the organic electronics device, as grain boundaries between crystallites act as traps for charges. Moreover, the contact between the electrodes and the organic film is diminished.

A very promising concept for the improvement of the morphological stability of low molecular weight materials is the spiro concept. This concept is based on the idea of connecting two molecular π-systems with equal or different functions (emission, charge transport) via a common sp3-hybridized atom.

9,9' (9H) Spirobifluorene (I)

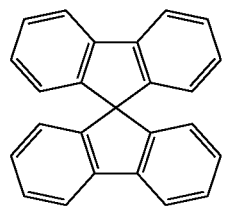

(1)

is the starting material for a group of substituted spirobifluorene compounds used today for application the field of organic electronics.

Spirobifluorenes substituted at at least one of positions 2, 2', 7 or 7' by a leaving group, i.e. a substituent which can be replaced to synthesize other molecules have been described in the prior art

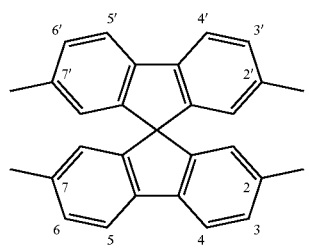

(2)

Compounds of this type which are fully symmetrically substituted in all para positions are usually obtained form spirobifluorene itself. Horizontally unsymmetrical spiro compounds wherein the substituents in 2 and 7 position are identical but differ from the substituents in the 2' and 7' position require a more complex strategy for their synthesis whereas vertically unsymmetrical spirobifluorenes wherein the substituents in 2 and 2' position are identical but differ from the substituents in 7 and 7' position can be accessed via the direct substitution of spirobifluorene again if the first two groups entering in 2 and 2' position control the substitution in 7 and 7' position to prevent simultaneous substitution at all 4 positions.

Salbeck et al in Adv. Pol. Sci. (2006), 199:83-142 discloses a number of possible synthesis routes for the manufacture of spirobifluorene derivatives with para-substituents but is totally silent as to spirobifluorene derivatives with substituents in the meta-positions 3, 3', 6 or 6'.

JP 2006/089585 discloses 3,6 and 3,6' dihydroxy-spirobifluorene. The 3,6 disubstituted compound is synthesized from fluorenone and 3,3'.dihydroxybiphenyl as starting materials, no synthesis of asymmetrical spirobifluorene derivatives being disclosed. A number of further substituted spirobifluorenes is disclosed in this reference, all of them containing a reactive group in at least two of the para positions, through which the molecules are incorporated as repeating units into a polymer chain.

WO02/77060 discloses substituted spirobifluorenes carrying reactive substituents in para position of the ring system.

According to Nijegorodov et al., Spectrochimica Acta Part A 56, 783-795 (2000) the delocalisation of the π-system along the four phenyl units in the para-substituted spirobifluorene derivatives leads to a weak triplet level (2.39 eV), whereas the impossibility to achieve such delocalisation in the meta-substituted derivatives would have to be expected to lead to a greater triplet level (2.76 eV), the energy level of which appears to be suitable to be preferably used with a blue phosphorescent emitter.

Accordingly, it was an object of the present invention to provide suitable precursors for the manufacture of meta-substituted spirobifluorene materials useful in the organic electronics area.

This object has been achieved with the compounds in accordance with claim 1. Preferred embodiments are described in the dependent claims and in the detailed description hereinafter.

The compounds in accordance with the present invention are characterized by the general formulae (3) (the ring system in formula (3) will be referred to as SBF hereinafter) or (4) (the ring system in formula (4) will hereinafter referred to as Open SBF)

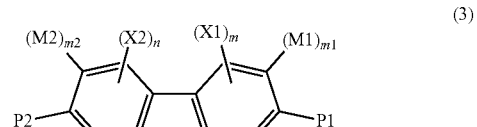

(3)

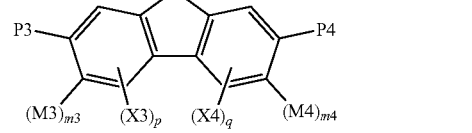

(4)

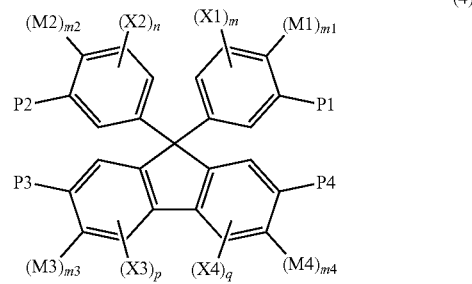

wherein

M1 to M4, which may be the same or different, represent halogen, —CN, —SCN, —OCN, $OR^1$, $SR^2$, —$B(OR^3R^4)$ or —O—$(SO_2)$—$R^5$, m1, m2, m3 and m4, which may be the same or different, are individually 0 or 1 and the sum of (m1+m2+m3+m4) represents an integer of from 1 to 3, $R^1$ represents $C_1$ to $C_{20}$ alkyl, $C_2$-$C_{20}$-alkenyl, $C_2$-$C_{20}$ alkinyl, arylalkyl, aryl or heteroaryl or may form an annealed ring system with other rings selected from cycloalkyl, aryl and heteroaryl rings, $R^2$ to $R^5$, which may be the same or different, represent hydrogen, $C_1$ to $C_{20}$ alkyl, $C_2$-$C_{20}$-alkenyl, $C_2$-$C_{20}$ alkinyl, arylalkyl, aryl or heteroaryl or may form an annealed ring system with other rings selected from cycloalkyl, aryl and heteroaryl rings, P1 to P4, which may be the same or different, represent hydrogen, $C_1$ to $C_{20}$ alkyl, $C_2$-$C_{20}$-alkenyl, $C_2$-$C_{20}$ alkinyl, arylalkyl, aryl or heteroaryl or may form an annealed ring system with other rings selected from cycloalkyl, aryl and heteroaryl rings, X1 to X4, which may be the same or different, represent, $C_1$ to $C_{20}$ alkyl, $C_2$-$C_{20}$-alkenyl, $C_2$-$C_{20}$ alkinyl, arylalkyl, aryl or heteroaryl or may form an annealed ring system with other rings selected from cycloalkyl, aryl and heteroaryl rings and m, n. p and q, which may be the same or different, are an integer of from 0 to 2.

Preferred compounds of formula (3) or (4) are those wherein M1 to M4 represent halogen, preferably F, Cl, Br or I, —CN, —$OR^1$, $SR^2$, —$B(OR^3R^4)$ or —O—$(SO_2)$—$R^5$.

Particularly preferred are compounds where at least one of M1 to M4 is Cl or Br, $OR^1$, $SR^2$ or —$B(OR^3R^4)$. Another group of preferred compounds in accordance with the present invention comprises at least two substituents M1 to M4 in meta-position, i.e. in 3,6, 3',6', 3,6' or 3',6 position, substitution in 3',6 or 3,6' position being particularly preferred.

Another group of preferred compounds in accordance with the present invention comprises three substituents M1 to M4.

The aforementioned preferred compounds may be characterized by the following formulae 3-1 to 3-5, of which 3-1 and 3-3 to 3-5 are particularly preferred:

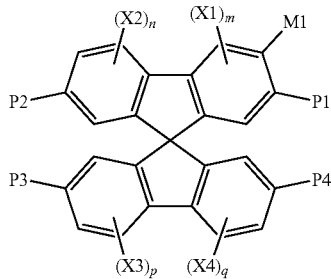

(3-1)

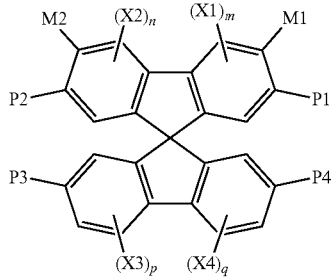

(3-2)

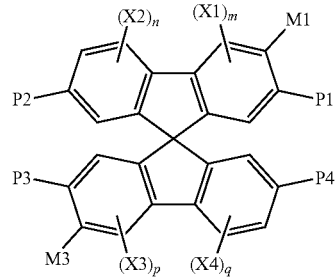

(3-3)

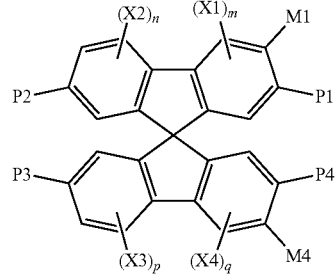

(3-4)

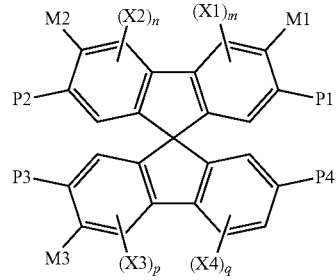

(3-5)

A further particularly preferred group of compounds in accordance with the present invention are compounds of formula 3-1 or 3-2 wherein M1 respectively M1 and M2 are halogen, preferably chlorine or bromine.

Another particularly preferred group of compounds is represented by formulae 3-1 to 3-5 wherein M1 to M4, which may be the same or different, are —CN, —SCN, —OCN, $OR^1$, $SR^2$, —$B(OR^3R^4)$ or —O—$(SO_2)$—$R^5$.

Still another preferred group of compounds in accordance with the present invention is characterized by formulae 3-3 to 3-5 wherein M1 to M4, which may be the same or different, are halogen, —CN, —SCN, —OCN, $OR^1$, $SR^2$, —$B(OR^3R^4)$ or —O—$(SO_2)$—$R^5$.

Another group of preferred compounds in accordance with the present invention is represented by formula 3-2 wherein at least one of M1 or M2 is selected from the group consisting of —CN, —SCN, —OCN, $OR^1$, $SR^2$, —$B(OR^3R^4)$ or —O—$(SO_2)$—$R^5$.

Compounds of formulae 3-7 or 3-8, wherein P1 to P4, X1 to X4 and m, n, p and q are as defined in claim 1

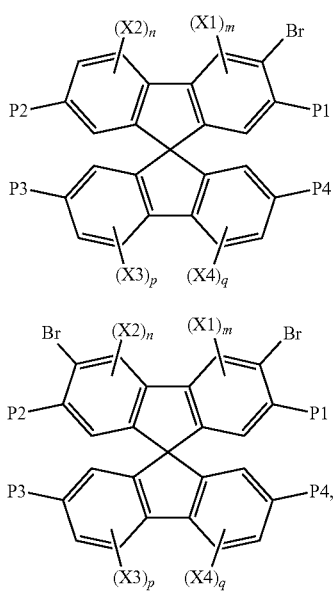

especially 3-Bromo-SBF and 3,6-dibromo-SBF may be mentioned as a further preferred group of compounds in accordance with the present invention.

The respective compounds with Open SBF instead of SBF represent another group of preferred compounds, which will be referred to hereinafter as 4-1 to 4-5.

P1 to P4 can be selected broadly from any of the above-mentioned groups, which share the common feature that the substituent is substantially inert under the reaction conditions used in the manufacture of materials suitable for use in the organic electronics area, i.e. they remain unchanged in these reactions. Preferred substituents P1 to P4 are hydrogen, $C_1$ to $C_{20}$ alkyl, $C_2$-$C_{20}$-alkenyl, $C_2$-$C_{20}$ alkinyl, arylalkyl, aryl or heteroaryl. Particularly preferably P1 to P4 represent hydrogen, $C_1$ to $C_8$ alkyl, $C_2$-$C_8$-alkenyl, $C_2$-$C_8$ alkinyl or aryl.

Substituents X1 to X4 are not subject to any limitation and thus can be broadly selected from the groups defined above.

3,3'-dibromo-SBF, 3-Chloro-SBF, 3,6-dichloro-SBF, 3,3'-dichloro-SBF, 3',6-dibromo-SBF, 3',6'-dibromo-SBF, 3',6-dichloro-SBF, 3',6'-dichloro-SBF, 3-alkoxy-SBF, 3,3'-di-alkoxy-SBF, 3,6'-dialkoxy-SBF, 3',6'-dialkoxy-SBF, preferably the respective dimethoxy, diethoxy or dipropyloxy compounds, 3-cyano-SBF, 3,3'-dicyano-SBF, 3,6'-dicyano-SBF, 3',6'-dicyano-SBF, 3-boronic acid ester-SBF or 3,6-Di-Boronic acid ester-SBF, all of which may be substituted by one or more substituents P1 to P4 and/or one or more of substituents X1 to X4 as defined above may be mentioned as a particularly preferred further group of compounds in accordance with the present invention.

Instead of having two or three identical substituents M1 to M4, another group of preferred compounds in accordance with the instant invention contains at least two different substituents M1 to M4, preferably selected from the groups as defined above, particularly preferred from F, Cl, Br or I, —CN, —$OR^1$, $SR^2$ or —$B(OR^3R^4)$, all of which may be substituted by one or more substituents P1 to P4 and/or one or more of substituents X1 to X4 as defined above. 3-bromo-3'-chloro-SBF derivatives may be mentioned as an example of this further preferred group of compounds in accordance with the present invention.

In all aforementioned preferred groups of compounds SBF may be replaced by Open SBF to yield the respective Open-SBF compounds.

The compounds in accordance with the present invention may be synthesized in accordance with various process routes which the skilled person will select in accordance with the specific needs. Generally, the compounds in accordance with the present invention are not easily accessible through introduction of the substituents directly into a SBF or Open SBF core as these routes generally yield the para-substituted products preferably due to their higher reactivity. Accordingly, the substituents M have to be introduced through suitable precursor substances e.g. fluorene derivatives, benzophenone derivatives or biphenyl derivatives, to mention only three examples, which are thereafter reacted to yield the SBF or Open SBF structure.

Thus, compounds of formula 3-1 may for example be obtained from fluorenone derivatives of formula

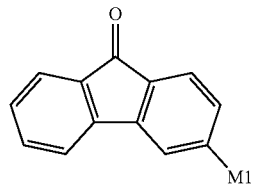

with suitable biphenyl compounds.

An alternative way to compounds of formula 3-2 to 3-5 is the reaction of substituted benzene compounds with suitable boronic acid derivatives to yield the desired compounds as shown in principle in the following reaction scheme for formula compounds of formula 3-4:

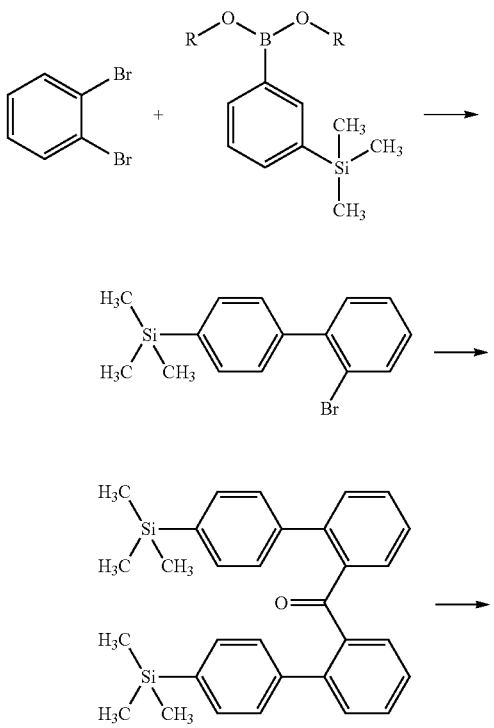

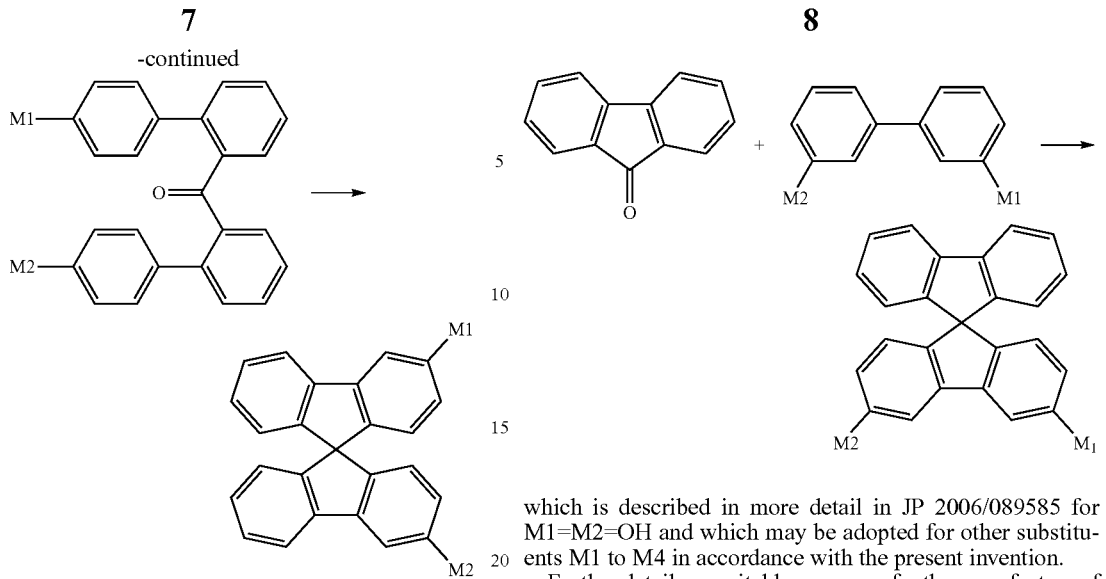

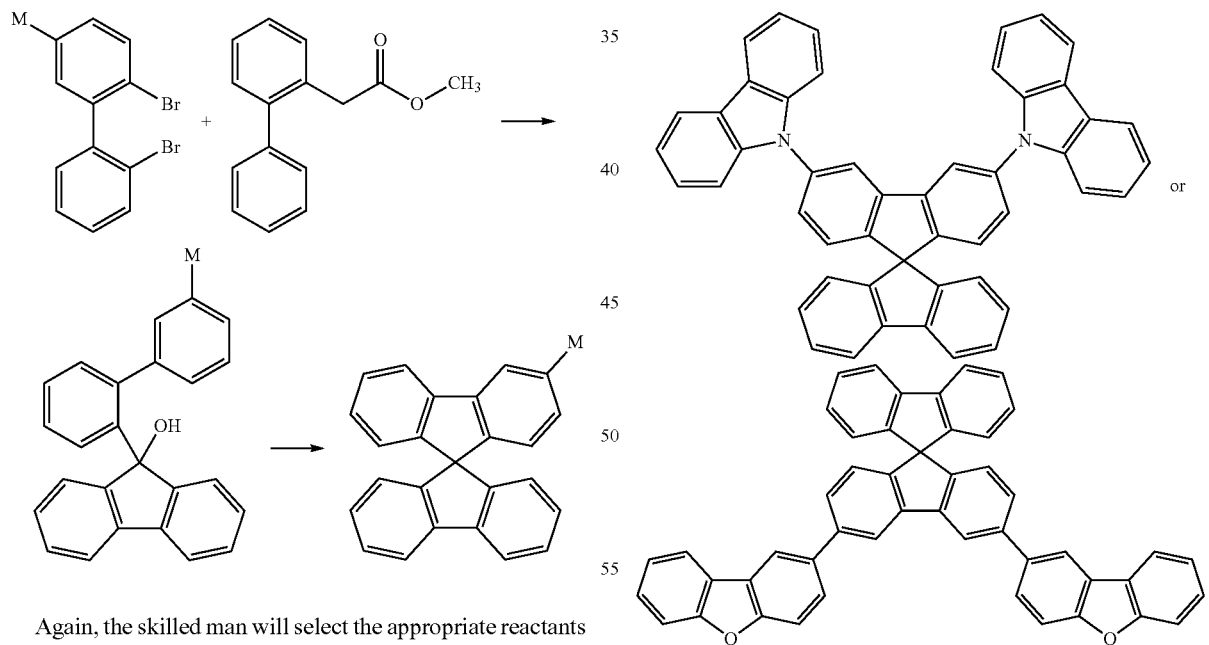

This method does not only lead to compounds of formula 3-4 but also to compounds of formula 3-3 and 3-5 and 4-2 to 4-5 respectively.

The skilled person will select the suitable reaction conditions and reactants for a specific synthesis based on his general knowledge of such reactions.

Another possible synthesis pathway may in general be described as follows:

Again, the skilled man will select the appropriate reactants and reaction conditions based on the individual synthesis intended. It is obvious that respective compounds with more than one substituent M can be obtained by suitable modification of the reactants.

Still another possibility for the synthesis of the compounds of the present invention is the reaction of fluorenones with suitable biphenyl compounds in accordance with the general reaction scheme (shown for the unsubstituted SBF-system and for formula 3-2)

which is described in more detail in JP 2006/089585 for M1=M2=OH and which may be adopted for other substituents M1 to M4 in accordance with the present invention.

Further details on suitable processes for the manufacture of the compounds in accordance with the present invention are given in the working examples hereinafter.

The compounds in accordance with the present invention are useful as intermediates for new materials in organic electronic systems like OLEDs or OFETs or the like. They could be used for the synthesis of new hosts for phosphorescent emitters or for electron transport or electron blocking materials as well as for the manufacture of hole transport or hole blocking materials.

Exemplary compounds which could be synthesized using the compounds of the present invention as educts are e.g.

to provide only two examples.

It is apparent to the skilled person that analogous compounds could be synthesized by selecting the appropriate compounds in accordance with the present invention as starting materials.

A further use is in the manufacture of ligands and transition metal complexes comprising such ligands, said complexes being useful in organic electronic devices.

Due to its leaving groups in the meta-positions relative to the bond linking the phenyl rings in the SBF or Open SBF unit the compounds in accordance with the instant invention open the way to ligands and complexes with an interesting emission spectrum preferably in the blue or near-blue region, which are not as easily available from para-substituted ligands and transition metal complexes comprising same.

WORKING EXAMPLES

Example 1

Synthesis of 3-Bromo-SBF

Step 1: Synthesis of 3-Bromofluorenone

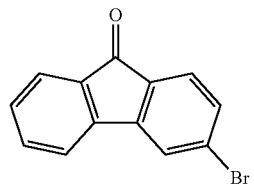 [SMILES: O=C1c2ccccc2-c2cc(Br)ccc21]

In a three ways flask 60 ml of water were added to 8.9 ml of hydrochloric acid (HCl, 37% w/w, 2.1 molar equivalents) and the medium was cooled to 0° C. NaNO$_2$ (1.5 molar equivalents), dissolved in 50 ml of water, was added dropwise at 0° C. At the end of the addition, 4-amino-2-bromobenzophenone (one equivalent, 15.0 g, 51.6 mmole) solubilised in a mixture of acetone/water (400/230 ml), was added carefully. After 30 minutes at room temperature, the mixture was warmed up and kept at 60° C. for 3 hours.

After extraction with methylene chloride and evaporation of the organic phase, a brown solid was recovered (17.4 g) and a flash chromatography is realized. The pure compound was recovered after crystallization with hexane (4.2 g, 32% yield).

Step 2: 3-bromo-SBF

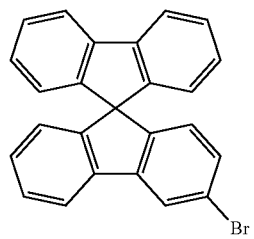 [SMILES: Brc1ccc2c(c1)-c1ccccc1C21c2ccccc2-c2ccccc21]

This compound was made in two steps from 3-bromofluorenone obtained in step 1. First, 2-bromobiphenyl (1.05 equivalents, 4.0 g, 16.5 mmol) is solubilised in 102 ml of anhydrous diethyl ether. This solution is cooled to −60° C. and n-BuLi (1.16 eq.) is added dropwise. After 10 min at this temperature, a white precipitate appeared which was redissolved while the medium was warmed to room temperature. 3-Bromofluorenone was then added and the reaction mixture was kept at 45° C. for one night.

After addition of NH$_4$Cl (5% aq., 260 ml) and extraction with diethyl ether, 7.0 g of an alcohol was obtained. This solid was solubilised in 141 ml of acetic acid and hydrolyzed by the addition of 78 ml of HCl/dioxane (10% mol, 20 eq.). After evaporation of the solvents, the solid was subjected to normal phase flash chromatography to afford 5.86 g of the target compound (94% yield).

Example 2

3-chloro-SBF

Step 1: 1-Bromo-7-chloro-biphenyl

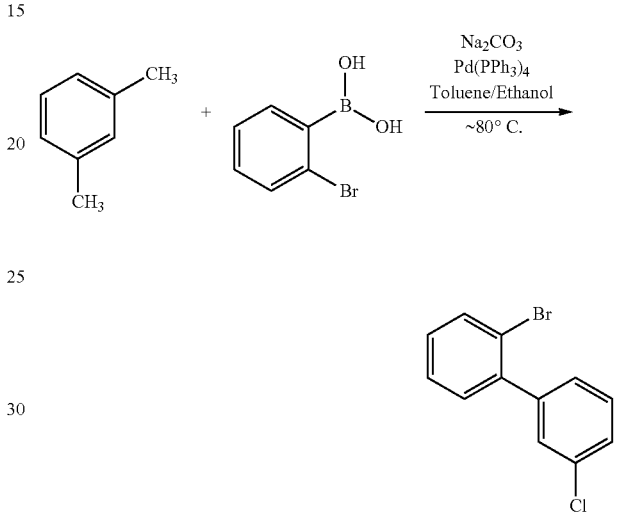

A 50-ml round-bottom flask under nitrogen atmosphere was charged sequentially with Pd(OAc)$_2$ (1.07 g, 0.0047 mol), PPh$_3$ (5.0 g, 0.0032 mol) and dioxane (35 ml). This mixture was added to a 500 ml round bottom flask already filled with 1-Chloro-3-iodobenzene (13.6 g, 0.056 mol) in dioxane (150 ml), 2N aqueous sodium carbonate (180 ml) and 2-Bromophenylboronic acid (12.3 g, 0.059 mol). This mixture was heated at reflux under N2 for 1.5 h and cooled to room temperature. The reaction medium was partitioned between water and ethyl acetate. The combined organic layers were washed with brine, dried over MgSO$_4$, and concentrated. The residue was purified by column chromatography (CH$_2$Cl$_2$/hexane) to afford the desired product with 76.6% yield.

Step 2: 3-chloro-SBF

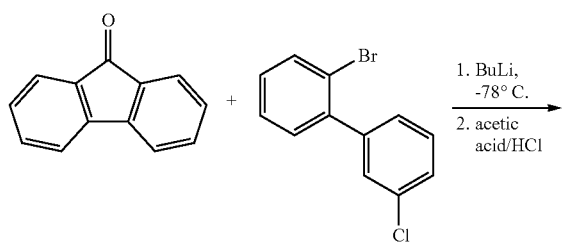

-continued

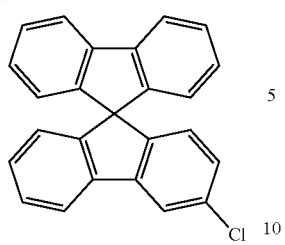

To a solution of 1-Bromo-7-Chloro-biphenyl (10 g, 0.037 mol) in anhydrous THF (100 ml) cooled to −78° C. a solution of 1.6 M n-BuLi in hexane (0.037 mol, 23.2 ml) was added dropwise. The reaction mixture was stirred at −78° C. for 1 h and a solution of fluorenone (0.031 mol, 5.58 g) in anhydrous THF (25 ml) was added dropwise. After addition, the mixture was allowed to warm to room temperature and stirred for 2 h. The mixture was quenched with saturated NH$_4$Cl (200 ml) and extracted with ethyl acetate (3*125 ml). The combined organic layers were washed with brine, dried over Na$_2$SO$_4$ (or MgSO$_4$) and concentrated in vacuo. The residue was purified by flash chromatography to afford the target compound with ~20% yield.

3,3'-dichloro-SBF and 3-Bromo-3'-chloro-SBF could be prepared in an analogous manner using 1-bromo-7-chloro-biphenyl.

The experimental conditions described in this Example 2 could also be used for the synthesis of other SBF-derivatives.

Thus, 3-Bromo-3'-chloro-SBF could be obtained by reacting 1-bromo-7-chloro-biphenyl with 3'-bromo-fluorenone according to the following reaction scheme:

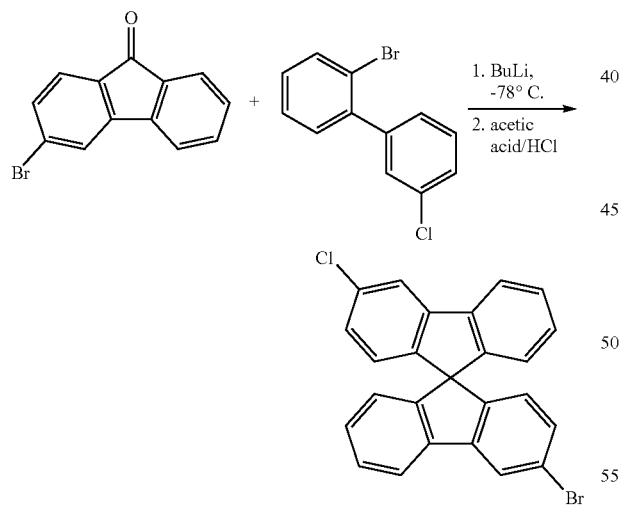

Example 3

3,6-dibromo-SBF 3,6-dibromo-fluorenone was synthesized following the method of Yong Cao et al, Adv. Mater. 2008, 20, 2359-2364 in accordance with the following reaction scheme:

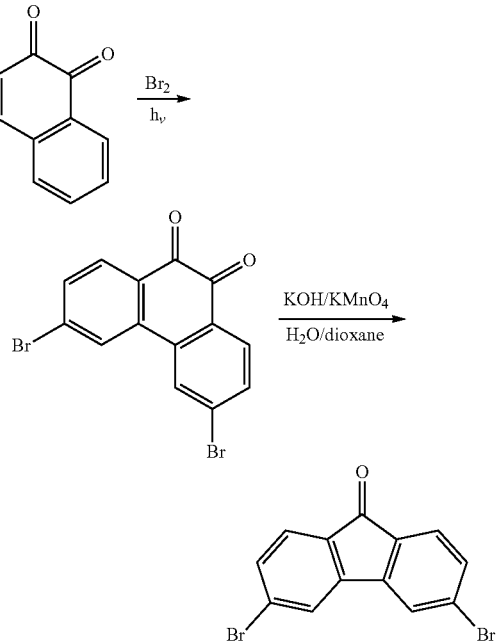

3,6-dibromo-fluorenone was reacted with 2-bromobiphenyl under the conditions given above in step 2 of Example 1 to obtain the target compound 3,6-dibromo-SBF in 48% yield Example 4

3,6-dibromo-3'-chloro-SBF

By using 3,6-dibromo-fluorenone instead of fluorenone under the conditions in accordance with working Example 2, 3,6-dibromo-3'-chloro-SBF can be obtained.

The foregoing working examples give exemplary synthesis processes for compounds in accordance with the present invention. It is apparent to the skilled person that he can obtain other compounds in accordance with the present invention by modifying the procedures or the reactants described.

The invention claimed is:
1. A compound of general formula (3)

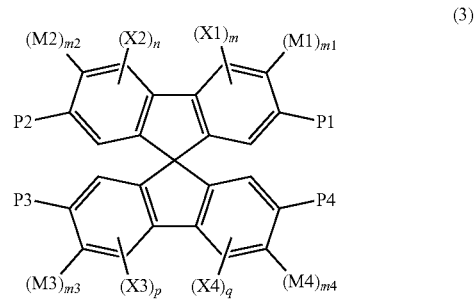

wherein
M1 to M4, which may be the same or different, represent halogen, —CN, —SCN, —OCN, OR$^1$, SR$^2$, —B(OR$^3$R$^4$) or —O—(SO$_2$)—R$^5$, wherein at least one of M1 to M4 represents halogen, m1, m2, m3 and m4, which may be the same or different, are individually 0 or 1 and the sum of (m1+m2+m3+m4) represents an integer of from 1 to 3

$R^1$ represents $C_1$ to $C_{20}$ alkyl, $C_2$-$C_{20}$-alkenyl, $C_2$-$C_{20}$ alkinyl, arylalkyl, aryl or heteroaryl or may form an annealed ring system with other rings selected from cycloalkyl, aryl and heteroaryl rings, $R^2$ to $R^5$, which may be the same or different, represent hydrogen, $C_1$ to $C_{20}$ alkyl, $C_2$-$C_{20}$-alkenyl, $C_2$-$C_{20}$ alkinyl, arylalkyl, aryl or heteroaryl or may form an annealed ring system with other rings selected from cycloalkyl, aryl and heteroaryl rings P1 to P4, which may be the same or different, represent hydrogen, $C_1$ to $C_{20}$ alkyl, $C_2$-$C_{20}$-alkenyl, $C_2$-$C_{20}$ alkinyl, arylalkyl, aryl or heteroaryl or may form an annealed ring system with other rings selected from cycloalkyl, aryl and heteroaryl rings, X1 to X4, which may be the same or different, represent, $C_1$ to $C_{20}$ alkyl, $C_2$-$C_{20}$-alkenyl, $C_2$-$C_{20}$ alkinyl, arylalkyl, aryl or heteroaryl or may form an annealed ring system with other rings selected from cycloalkyl, aryl and heteroaryl rings and m, n. p and q, which may be the same or different, are an integer of from 0 to 2.

2. A compound in accordance with claim 1 wherein M1 to M4, which may be same or different, represent halogen, —CN, —$OR^1$ $^{SR2}$, —$B(OR^3R^4)$ or —O—($SO_2$)—$R^5$, where $R^1$ to $R^5$ are as defined in claim 1.

3. A compound in accordance with claim 1, wherein at least one of M1 to M4 is Cl or Br, $OR^1$, $SR^2$ or —$B(OR^3R^4)$, where $R^1$ to $R^4$ are as defined in claim 1.

4. A compound in accordance with claim 1, having the formulae 3-1 to 3-5

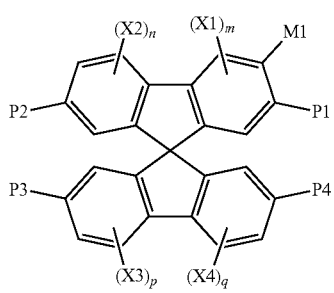

(3-1)

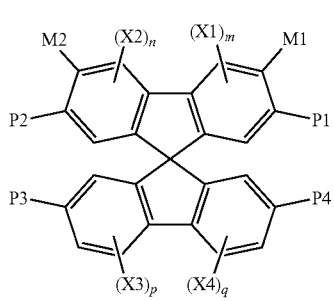

(3-2)

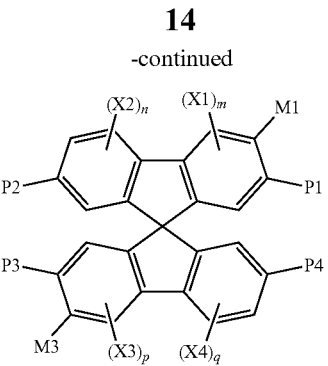

(3-3)

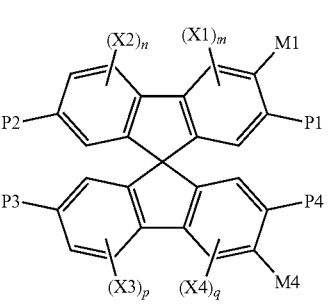

(3-4)

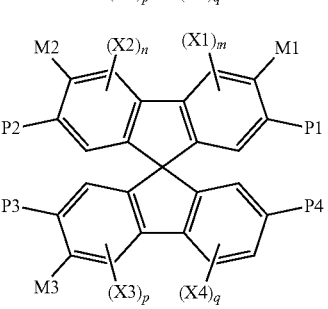

(3-5)

wherein M1 to M4, P1 to P4, X1 to X4, R' to $R^5$ and m, n, p and q have the meanings as defined in claim 1.

5. A compound of formulae 3-3 to 3-5 in accordance with claim 4 wherein M1 to M4, which may be the same or different, are selected from the group consisting of halogen, —CN, —SCN, —OCN, $OR^1$, $SR^2$, —$B(OR^3R^4)$ or —O—($SO_2$)—$R^5$,.

6. A compound in accordance with formula 3-2 in accordance with claim 4 wherein at least one of M1 or M2 is selected from the group consisting of —CN, —SCN, —OCN, $OR^1$, $SR^2$, —$B(OR^3R^4)$ or —O—($SO_2$)—$R^5$.

7. A compound in accordance with claim 1 wherein P1 to P4 are hydrogen, $C_1$ to $C_{20}$ alkyl, $C_2$-$C_{20}$-alkenyl, $C_2$-$C_{20}$ alkinyl, arylalkyl, aryl or heteroaryl.

8. A compound in accordance with claim 1, having the formulae 3-7 or 3-8, wherein P1 to P4, X1 to X4 and m, n, p and q are as defined in claim 1

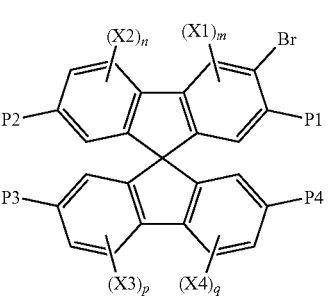

(3-7)

-continued

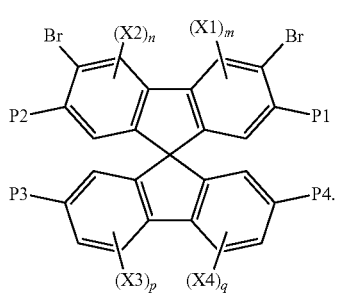

(3-8)

9. 3-Bromo-9,9'-spirobifluorenyl and 3,6-Dibromo-9,9'-spirobifluorenyl.

10. A compound in accordance with claim 4, selected from the group consisting of 3,3'-dibromo-SBF, 3-Chloro-SBF, 3,6-dichloro -SBF, 3,3'-dichloro-SBF, 3',6-dibromo-SBF, 3',6'-dibromo-SBF, 3',6-dichloro-SBF, all of which may be substituted by one or more substituents P1 to P4 and/or one or more of substituents X1 to X4 and wherein SBF denotes a 9,9'-(9H)-spirobifluorenyl group.

11. A compound in accordance with claim 1 wherein M1 to M4 represent F, Cl, Br or I.

* * * * *